(12) United States Patent
Dudding et al.

(10) Patent No.: US 10,472,157 B1
(45) Date of Patent: Nov. 12, 2019

(54) PATHOGEN ELIMINATING ARTICLE

(71) Applicant: CLAW Biotech Holdings LLC, Des Peres, MO (US)

(72) Inventors: Jeffery L. Dudding, Center, MO (US); Amod P. Paranjpe, Augusta, MO (US)

(73) Assignee: Claw Biotech Holdings LLC, Des Peres, MO (US)

( * ) Notice: Subject to any disclaimer, the term of this patent is extended or adjusted under 35 U.S.C. 154(b) by 510 days.

(21) Appl. No.: 15/204,522

(22) Filed: Jul. 7, 2016

Related U.S. Application Data

(62) Division of application No. 14/826,833, filed on Aug. 14, 2015, now abandoned.

(51) Int. Cl.
*B32B 1/02* (2006.01)
*B32B 15/01* (2006.01)
(Continued)

(52) U.S. Cl.
CPC .......... *B65D 81/28* (2013.01); *A01N 25/26* (2013.01); *A01N 59/16* (2013.01); *A47J 47/02* (2013.01); *B32B 1/02* (2013.01); *B32B 1/08* (2013.01); *B32B 7/10* (2013.01); *B32B 15/01* (2013.01); *B32B 15/013* (2013.01); (Continued)

(58) Field of Classification Search
CPC ..... B32B 15/01; B32B 15/013; B32B 15/015; B32B 15/04; B32B 15/043; B32B 15/017; B32B 1/02; B32B 1/08; B32B 7/10; B32B 15/08; Y10T 428/12917; Y10T 428/12924; Y10T 428/12972; Y10T 428/12979; Y10T 428/12993; Y10T 428/12944; Y10T 428/12903; Y10T 428/13; Y10T 428/2495; Y10T 428/26; Y10T 428/14; Y10T 428/12806; Y10T 428/12826; Y10T 428/12854; Y10T 428/12994; Y10T 428/12937; Y10T 428/1266; Y10T 428/12611; Y10T 428/12569; B65D 1/40; B65D 43/02; B65D 85/30; B65D 1/28; B65D 9/30; B65D 81/28; B65D 43/0202; A47J 47/02; A01N 59/16; A01N 25/26;
(Continued)

(56) References Cited

U.S. PATENT DOCUMENTS 3,966,426 A   6/1976   McCoy et al.
4,646,935 A   3/1987   Ulam
(Continued)

FOREIGN PATENT DOCUMENTS

CN   201055998 Y   5/2008
CN   103911540 A   7/2014
(Continued)

OTHER PUBLICATIONS

Hobman et al., Bacterial antimicrobial metal ion resistance, Journal of Medical Microbiology, dated Nov. 2014, pp. 471-497.
(Continued)

*Primary Examiner* — Michael E. La Villa
(74) *Attorney, Agent, or Firm* — Armstrong Teasdale LLP

(57) ABSTRACT

An article including a first layer of a shielding material comprising a first surface and an opposite second surface. The article also includes an core material coupled to the first surface, wherein the core material is configured to eliminate pathogens located on the second surface.

13 Claims, 4 Drawing Sheets

(51) Int. Cl.
| | |
|---|---|
| *B32B 15/04* | (2006.01) |
| *B65D 1/40* | (2006.01) |
| *B65D 1/28* | (2006.01) |
| *B65D 43/02* | (2006.01) |
| *A47J 47/02* | (2006.01) |
| *C22C 27/04* | (2006.01) |
| *B65D 81/28* | (2006.01) |
| *B65D 1/02* | (2006.01) |
| *B65D 85/30* | (2006.01) |
| *B65D 6/14* | (2006.01) |
| *A01N 59/16* | (2006.01) |
| *A01N 25/26* | (2006.01) |
| *B32B 1/08* | (2006.01) |
| *B32B 7/10* | (2006.01) |
| *B32B 15/08* | (2006.01) |
| *C22C 18/00* | (2006.01) |
| *C22C 19/05* | (2006.01) |
| *C23C 30/00* | (2006.01) |

(52) U.S. Cl.
CPC .......... *B32B 15/015* (2013.01); *B32B 15/017* (2013.01); *B32B 15/04* (2013.01); *B32B 15/043* (2013.01); *B32B 15/08* (2013.01); *B65D 1/0207* (2013.01); *B65D 1/28* (2013.01); *B65D 1/40* (2013.01); *B65D 9/30* (2013.01); *B65D 43/02* (2013.01); *B65D 43/0202* (2013.01); *B65D 85/30* (2013.01); *C22C 18/00* (2013.01); *C22C 19/051* (2013.01); *C22C 27/04* (2013.01); *C23C 30/00* (2013.01); *C23C 30/005* (2013.01); *Y10T 428/1266* (2015.01); *Y10T 428/12569* (2015.01); *Y10T 428/12611* (2015.01); *Y10T 428/12806* (2015.01); *Y10T 428/12826* (2015.01); *Y10T 428/12854* (2015.01); *Y10T 428/12903* (2015.01); *Y10T 428/12917* (2015.01); *Y10T 428/12924* (2015.01); *Y10T 428/12937* (2015.01); *Y10T 428/12944* (2015.01); *Y10T 428/12972* (2015.01); *Y10T 428/12979* (2015.01); *Y10T 428/12993* (2015.01); *Y10T 428/13* (2015.01); *Y10T 428/14* (2015.01); *Y10T 428/2495* (2015.01); *Y10T 428/26* (2015.01)

(58) Field of Classification Search
CPC ....... C22C 19/051; C22C 18/00; C22C 27/04; C23C 30/00; C23C 30/005
See application file for complete search history.

(56) References Cited

U.S. PATENT DOCUMENTS

| | | |
|---|---|---|
| 6,267,830 B1 | 7/2001 | Groll |
| 6,929,705 B2 | 8/2005 | Myers et al. |
| 7,488,444 B2 * | 2/2009 | Furst .................. B22F 3/16 |
| | | 148/423 |
| 7,906,221 B2 | 3/2011 | Groll |
| 8,133,596 B2 | 3/2012 | Groll |
| 8,609,036 B2 | 12/2013 | Fuller et al. |
| 8,723,308 B2 | 5/2014 | Yang et al. |
| 8,778,408 B2 | 7/2014 | Hirota et al. |
| 9,162,013 B2 | 10/2015 | Guggenbichler et al. |
| 9,675,079 B1 * | 6/2017 | Dudding ............. C22C 27/04 |
| 2009/0178410 A1 | 7/2009 | Straza |
| 2010/0061884 A1 | 3/2010 | Clark et al. |
| 2012/0225312 A1 | 9/2012 | Chin et al. |
| 2014/0224519 A1 | 8/2014 | Mallak et al. |
| 2015/0086497 A1 | 3/2015 | Niki et al. |
| 2015/0086597 A1 | 3/2015 | Mallak et al. |
| 2015/0290042 A1 | 10/2015 | Freer et al. |
| 2016/0186295 A1 | 6/2016 | Oishi et al. |

FOREIGN PATENT DOCUMENTS

| | | |
|---|---|---|
| KR | 20010088990 A | 9/2001 |
| WO | 2012045308 A1 | 4/2012 |

OTHER PUBLICATIONS

Romanszki et al., Polystyrene films as barrier layers for corrosion protection of copper and copper alloys, Bioelectrochemistry, dated 2014, pp. 7-14.

Research reveals 'halo' effect of copper surfaces, http://ww.cleanroomtechnology.com, date retrieved Jun. 24, 2015, pp. 2.

Zhu Libin et al., "Antimicrobial Activity of Different Copper Alloy Surfaces Against Copper Resistant and Sensitive *Salmonella enterica*"; Food Microbiology; vol. 30 2012; pp. 303-310.

* cited by examiner

PATHOGEN ELIMINATING ARTICLE

CROSS REFERENCE TO RELATED APPLICATIONS

This application is a divisional of U.S. patent application Ser. No. 14/826,833, filed Aug. 14, 2015, titled Pathogen Eliminating Article and Methods of Manufacturing the Same, the content of which is incorporated by reference in its entirety.

BACKGROUND

The present disclosure is directed generally to methods and apparatus related to antimicrobial products for use in neutralizing harmful pathogens and, more particularly, to methods and apparatus that include an antimicrobial alloy core encased in a protective shielding that neutralizes the pathogens without physical contact.

Currently, there exists a large variety of strains of antibiotic resistant virulent microbes. Such microbes are known to cause a variety of diseases. Microbes like methicillin-resistant *Staphylococcus aureus* strain ATCC 6538, which, if left untreated, can lead to sickness and even death. This problem is especially prevalent in locations (hospitals, hotels, public schools, elderly homes, etc.) where infectious microbes can easily be spread among its inhabitants. There is a need to frequently disinfect surfaces that people may come into contact with. Additionally, microbes such as *E. Coli* and *Salmonella* are known to be found in food manufacturing and preparation facilities where the possibility exists for the microbes to be located on surfaces that contact food items before they are packaged or prepared for human consumption. Such locations and facilities require frequent cleaning using antimicrobial agents to disinfect surfaces that may harbor infectious microbes.

At least some known antimicrobial agents include chemical antimicrobial agents, e.g., disinfectants. However, at least some chemical antimicrobial agents may be harmful to both the environment and the person coming into contact with them. Also, at least some chemical antimicrobial agents lose their antimicrobial effectiveness within a relatively short time period as the microbes become resistant to the agent.

Another known antimicrobial agent includes an antimicrobial metallic alloy used to disinfect a surface having harmful microbes. Such alloys use a natural oligodynamic effect to reduce or eliminate the microbes that directly contact the surface of the alloy. However, at least some known antimicrobial metallic alloys are formed from materials that oxidize relatively easily, especially when exposed to external elements such as the open air or chemical antimicrobial agents that may be used to further eliminate the microbes. Additionally, the materials that make up many known antimicrobial metallic alloys are relatively soft and may be susceptible to marring, fragmentation, and other damage during use. Such qualities are undesirable, especially in food preparation products because of the risk of contamination, which may lead to illness.

BRIEF DESCRIPTION

In one aspect, an article includes a first layer of a shielding material comprising a first surface and an opposite second surface. The article also includes a core material coupled to the first surface, wherein the core material is configured to eliminate pathogens located on the second surface.

In another aspect, a method of disinfecting a surface by eliminating pathogens from the surface using an antimicrobial article is provided. The method includes forming an antimicrobial core material and forming at least one layer of a non-antimicrobial shielding material including a first surface and an opposite second surface. The method also includes coupling the antimicrobial core material to the first surface such that the antimicrobial core material disinfects the second surface without contacting pathogens thereon.

In yet another aspect, a food storage container is provided. The food storage container includes a plurality of walls defining a cavity configured to receive a food item therein. At least one of the plurality of walls is formed from an article comprising a first layer of a non-antimicrobial shielding material comprising a first surface and an opposite second surface, and an antimicrobial core material coupled to the first surface. The antimicrobial core material is configured to eliminate pathogens located on the second surface and within the cavity.

DETAILED DESCRIPTION

Described herein is an antimicrobial article including an antimicrobial metallic alloy core and a non-antimicrobial shield coupled to the antimicrobial core. The antimicrobial core includes an antimicrobial alloy containing a minimum of 50% of at least one of copper/copper alloys, silver, gold, or molybdenum. The antimicrobial article may include any antimicrobial alloy, such as, for example, antimicrobial copper/copper alloys, identified by the United States Environmental Protection Agency (EPA). The non-antimicrobial shield is fabricated from a non-antimicrobial material, such as, but not limited to stainless steel and serves as a protective layer to the antimicrobial core providing strength, physical and chemical durability, and stainless qualities. As described in further detail below, the antimicrobial article provides an antimicrobial property due to a "halo effect" from electromagnetic energy produced by the protected antimicrobial alloy core that disinfects the surface of the shield opposite the antimicrobial core without contacting the bacterium located thereon and within a relatively short period of time.

Additionally, as used herein, the term "pathogens" is meant to describe any harmful virus, bacteria, or fungus that may cause disease. For example, a pathogen may be any of methicillin-resistant *Staphylococcus aureus* strain ATCC 6538, and the like. More specifically, pathogens commonly found in healthcare environments include *Acinetobacter baumannii, Bacteroides fragilis, Burkholderia cepacia, Clostridium difficile, Clostridium sordellii*, Carbapenem-resistant Enterobacteriaceae, *Enterococcus faecalis, Escherichia coli*, Hepatitis A, Hepatitis B, Hepatitis C, Human Immunodeficiency Virus, Influenza, *Klebsiella pneumonia*, Methicillin-resistant *Staphylococcus aureus,*

*Morganella morganii, Mycobacterium abscessus*, Norovirus, Psuedomonas *aeruginosa, Staphylococcus aureus, Stenotrophomonas maltophilia, Mycobacterium tuberculosis*, Vancomyin-resistant *Staphylococcus aureus*, and Vancomycin-resistant Enterococci.

Furthermore, pathogens commonly found in food production that are eliminated by the "halo effect" include *Bacillus cereus*, Botulism, *Campylobacter, Clostridium perfringens, Listeria, Salmonella, Shigella, Vibrio vulnificus* and *Vibrio parahaemolyticus*. Many known pathogens eliminated by the "halo effect" may be found in many different environments.

The terms "including", "comprising" and variations thereof, as used in this disclosure, mean "including, but not limited to", unless expressly specified otherwise.

The terms "a", "an", and "the", as used in this disclosure, means "one or more", unless expressly specified otherwise. The terms "about" or "approximately" refer to within +/−10%, when referring to a percentage.

Although process steps, method steps, or the like, may be described in a sequential order, such processes and methods may be configured to work in alternate orders. In other words, any sequence or order of steps that may be described does not necessarily indicate a requirement that the steps be performed in that order. The steps of the processes or methods described herein may be performed in any order that facilitates operation of the method.

Figure 1:
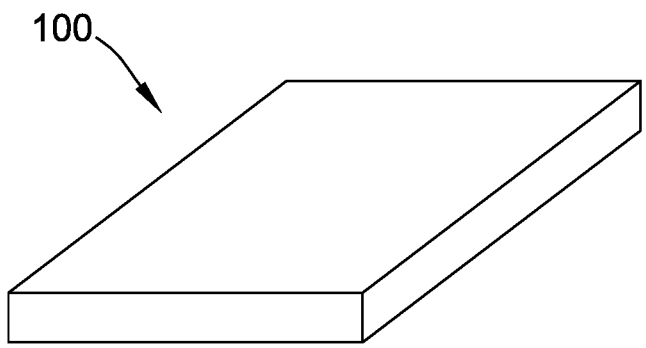
FIG. 1 is a perspective view of an exemplary antimicrobial article.

Referring now to FIG. 1, a perspective view of an exemplary antimicrobial article 100 is illustrated. Antimicrobial article 100 includes any product used in, for example, healthcare, extended care, residential or commercial facilities, public or private facilities, public or private vehicles, food manufacturing and preparation locations, medical and other health care devices, refrigeration units, HVAC (heating, ventilation and air conditioning) equipment, or anywhere else where pathogens may be transferred through contact of or exposure to a surface.

For example, such products may include, but are not limited to, e.g., a bed or any part thereof (e.g., a bedrail, a footboard, an over-bed table, or the like), a table or any part thereof, a handle or any part thereof (e.g., a knob, a pull bar, a push plate, a pull plate, a fluted knob, a knurled knob, a push/pull knob, a T-handle, a tapered knob, a ball knob, or the like), a handrail, a wall panel, a cart or any part thereof (e.g., a hospital cart, a computer cart, a record cart, a phlebotomy cart, a shopping cart, or the like), a kick plate, a mop plate, a stretcher plate, a sink or any part thereof, a spigot, a drain, a faucet, a drain control lever, a water fountain, a bubbler head, a drain strainer, an alcohol sanitizer dispenser, a paper towel holder, a facial tissue holder, a toilet paper holder, an air hand dryer, a control and/or push button on an air hand dryer, a hydrotherapy tank (e.g., a whirlpool tank), a shell, a cover, a headrest, a grab bar (e.g., in a bathroom shower or bathtub), a panic bar on a door, a towel bar, a showerhead, a countertop, a hinge, a lock, a latch, trim, a floor stop, a protector guard, a toilet, toilet hardware, a urinal, urinal hardware, a lever, a push button, a toilet seat inlay for lifting of seat, a vertical locking arm, a vertical cover guard, a protection bar, a light switch, a switch plate, a chair, an armrest, a chair frame, a thermostat cover, a telephone handset, a keypad, any kitchen surface (where the kitchen surface may include any non-prep food area, so that food does not contact the antimicrobial surface), a microwave handle, a refrigerator handle, a stove handle, a cabinet door, a backsplash, a hood, an appliance control knob, a floor tile, a ceiling tile, a wall tile, an instrument handle, a housing/control/handle for a monitoring system, a stand, a light fixture, an intravenous (IV) pole, a base, a hanger, a clip, a tray, a bedpan, a walker, a wheelchair or any part thereof, a computer or any part thereof, exercise/rehabilitation/physical therapy equipment or any part thereof, a chart holder, clipboard, a shelf (e.g., storage shelf), a child seat or any part thereof, an ATM machine or any part thereof, an elevator or any part thereof, a soap holder or any part thereof, a soap dispenser or any part thereof, a toilet paper dispenser or any part thereof, a window or any part thereof, a light switch or any part thereof, a laundry hamper or any part thereof, a container or canister or any part thereof, a magazine rack, a signage, a coat rack and hook, a shower curtain ring, a radiator cover, a badge clip, a name tag, a vending machine or any part thereof, a gang wall plate (e.g., toggle switch, rocker switch, duplex outlet, or the like, or any combination of the foregoing), a tile (a self-adhesive tile or a grouted tile), a flat sheet for a baby changing table, a toilet brush cleaner, and the like.

Additionally, food processing and production items could include air knives, aseptic packaging/processing system equipment, bacon hangers, storage drums, food storage bins and containers, blanchers, deboning equipment, brine storage vessels, sanitary wall panels, sanitary ceiling panels, canning equipment, carts, casters and wheels, chillers, clean in place equipment, conveyor equipment, cookers, cooling tunnels, cutting boards, dispensers, doors, dough equipment, dryers, dumpers, elevators, evaporators, sanitary expansion joints, evaporators, feeders, filling equipment, freezers, fruit preparation equipment, fryers, grinders, homogenizers, hoppers, kettles, kneaders, laboratory tools and equipment, meat processing tools and equipment, mixers, ovens, packaging equipment, paddles, pails, pasteurizers, peelers, pump housings, roasters, scales, food preparation tables, silos, autoclaves, strainers, tanks, trays, and water coolers. HVAC equipment includes air scrubbers, air handlers, cooling towers, condensate drip pans, ductwork, dehumidifiers, fan housings, filters, louvers, column dampers, and turning vanes.

Furthermore, article 100 may include products for use in hospitals, operating rooms, ambulatory surgery centers, and nursing homes. For example, such products include health care equipment, such as but not limited to surgical instruments, surgical instrument storage containers, surgical implants (joint replacements), surgical screws, surgical plates, tables, stools, cabinetry, flooring, inflow and return ducts, back tables, Mayo stands, IV poles, biohazard storage locations, lockers, waiting rooms, autoclaves, scrub sinks, stretchers, MRI/CT imaging facilities, dental facilities, veterinary facilities, laboratory facilities (clinical and research), and the like.

Figure 2:
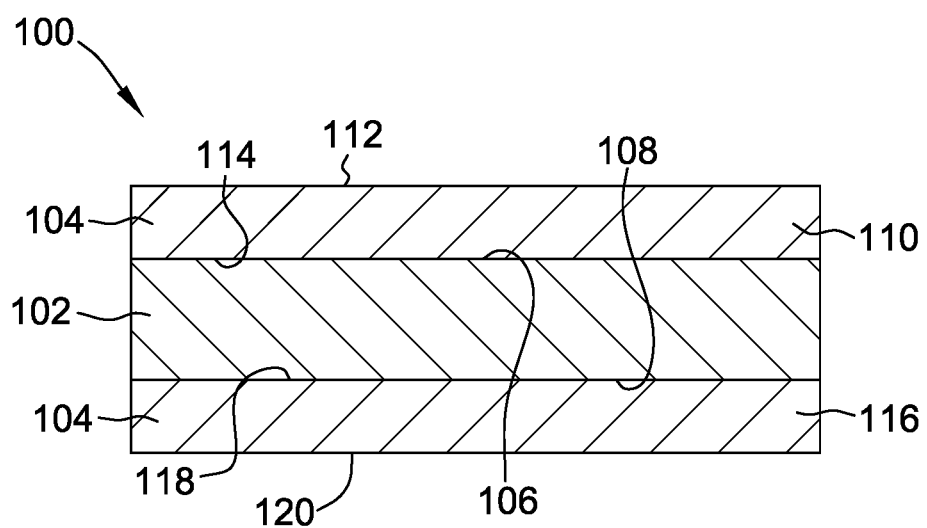
FIG. 2 is a cross-sectional view of the antimicrobial article shown in FIG. 1.
Figure 3:
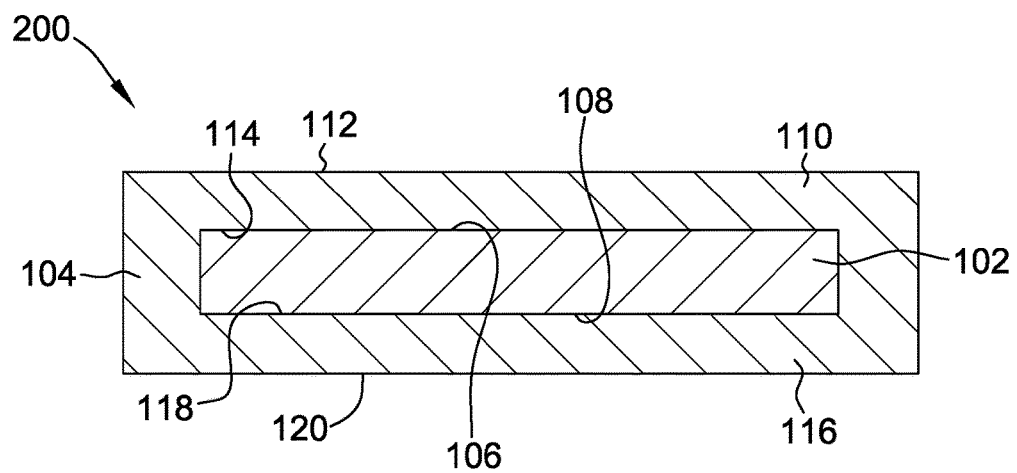
FIG. 3 is a cross-sectional view of another antimicrobial article.

FIG. 2 is a cross-sectional view of antimicrobial article 100 illustrating a layering of an antimicrobial core 102 and a non-antimicrobial shield 104. FIG. 3 is a cross-sectional view of another antimicrobial article 200 illustrating antimicrobial core 102 encased within non-antimicrobial shield 104 to prevent exposure of antimicrobial core 102, as described in further detail below.

In the exemplary embodiment, antimicrobial article 100 includes antimicrobial core 102 coupled to a surface of non-antimicrobial shield 104 such that antimicrobial core 102 kills any pathogens located on a surface of non-antimicrobial shield 104 opposite antimicrobial core 102 without directly contacting the pathogens. More specifically antimicrobial core 102 includes a first surface 106 and a second surface 108, and non-antimicrobial shield 104 includes a first layer 110 having a third surface 112 and a fourth surface 114 and a second layer 116 having a fifth surface 118 and a sixth surface 120.

Antimicrobial core 102 is coupled to first layer 110 of non-antimicrobial shield 104 such that first surface 106 is coupled in a face-to-face relationship with fourth surface 114. In such a configuration, the "halo effect" antimicrobial property of antimicrobial core 102 emits electromagnetic energy that penetrates non-antimicrobial shield 104 and disinfects third surface 112 without directly contacting the pathogen located on third surface 112 within a time period of approximately 2-3 hours. In the exemplary embodiment, antimicrobial core 102 effectively kills pathogens within approximately 2-3 hours of the pathogens being exposed to the electromagnetic energy emitted by antimicrobial core 102. Article 100 may be located in any location that is likely to come within an estimated effective range of the electromagnetic energy's "halo effect". In the exemplary embodiment, experimentation has demonstrated that the "halo effect" of antimicrobial core 102 exhibits up to 70% effectiveness against pathogen microbes at a distance of up to 50.0 centimeters (19.68 inches). Furthermore, the effectiveness against pathogen microbes has been shown to be independent of both shielding material and thickness.

In the exemplary embodiment, article 100 includes second layer 116 coupled to antimicrobial core 102 such that second surface 108 is coupled in a face-to-face relationship with fifth surface 114. In such a configuration, the "halo effect" disinfects both third and sixth surfaces 112 and 120 within the same time period. As such, in the exemplary embodiment, article 100 includes only three layers of material, with antimicrobial core 102 positioned between layers of non-antimicrobial shield, and no additional layers of material are provided in article 100. Alternatively, article 100 includes only first layer 110 of non-antimicrobial shield 104. Generally, non-antimicrobial shield 104 serves as a protective layer between antimicrobial core 102 and the external environment. In the exemplary embodiment, antimicrobial core 102 and non-antimicrobial shield 104 are coupled via any known welding process. Alternatively, antimicrobial core 102 and non-antimicrobial shield 104 are coupled via any manner, such as adhesive bonding. In another embodiment, shown in FIG. 3, non-antimicrobial shield 104 completely encases antimicrobial core 102 such that antimicrobial core 102 is prevented from any exposure to the atmosphere or external elements.

In the exemplary embodiment, non-antimicrobial shield 104 is fabricated from a metal or metallic alloy of stainless steel, nickel, aluminum, sheet metal, tin, or any combination thereof. Preferably, non-antimicrobial shield 104 is fabricated from a commercially available stainless steel alloy such as, but not limited to one of 304, 304L, 316, and 316L alloys. Alternatively, non-antimicrobial shield 104 is fabricated from at least one of a hard plastic material, an elastomeric material, and a ceramic material. Generally, non-antimicrobial shield 104 is fabricated from any material that facilitates protecting antimicrobial core 102 from external environmental effects such as impacts, chopping, cutting, chemical wipes, and the like. As such, non-antimicrobial shield 104 prevents any outside substance from contacting antimicrobial core 102. In the exemplary embodiment, non-antimicrobial shield 104 is more than 10% of a total material of antimicrobial article 100. More specifically, non-antimicrobial shield 104 makes up between approximately 10% to approximately 99% of a total material of antimicrobial article 100. Even more specifically, non-antimicrobial shield 104 makes up between approximately 10% to approximately 50% of a total material of antimicrobial article 100. Alternatively, non-antimicrobial shield 104 consists of any percentage of material for article 100.

In the exemplary embodiment, antimicrobial core 102 is fabricated from an antimicrobial alloy including any combination of copper/copper alloys, gold, silver, and molybdenum. More specifically, antimicrobial core 102 includes an antimicrobial active component and a non-antimicrobial inactive component. As described above, the active component includes at least one of copper, gold, silver, and molybdenum. Additionally, the active component makes up at least 10% of a total material of antimicrobial core 102. More specifically, the active component makes up at least 50% of a total material of antimicrobial core 102. Even more specifically, the active component makes up between approximately 60% to approximately 90% of a total material of antimicrobial core 102. The inactive component includes at least one of nickel and zinc. The inactive component makes up between approximately 1% to approximately 50% of a total material of antimicrobial core 102. Overall, in the exemplary embodiment, antimicrobial core 102 makes up between approximately 10% to approximately 90% of a total material of antimicrobial article 100. For example, in the exemplary embodiment, antimicrobial core 102 includes an alloy of approximately 70% copper and approximately 30% nickel.

Figure 4:
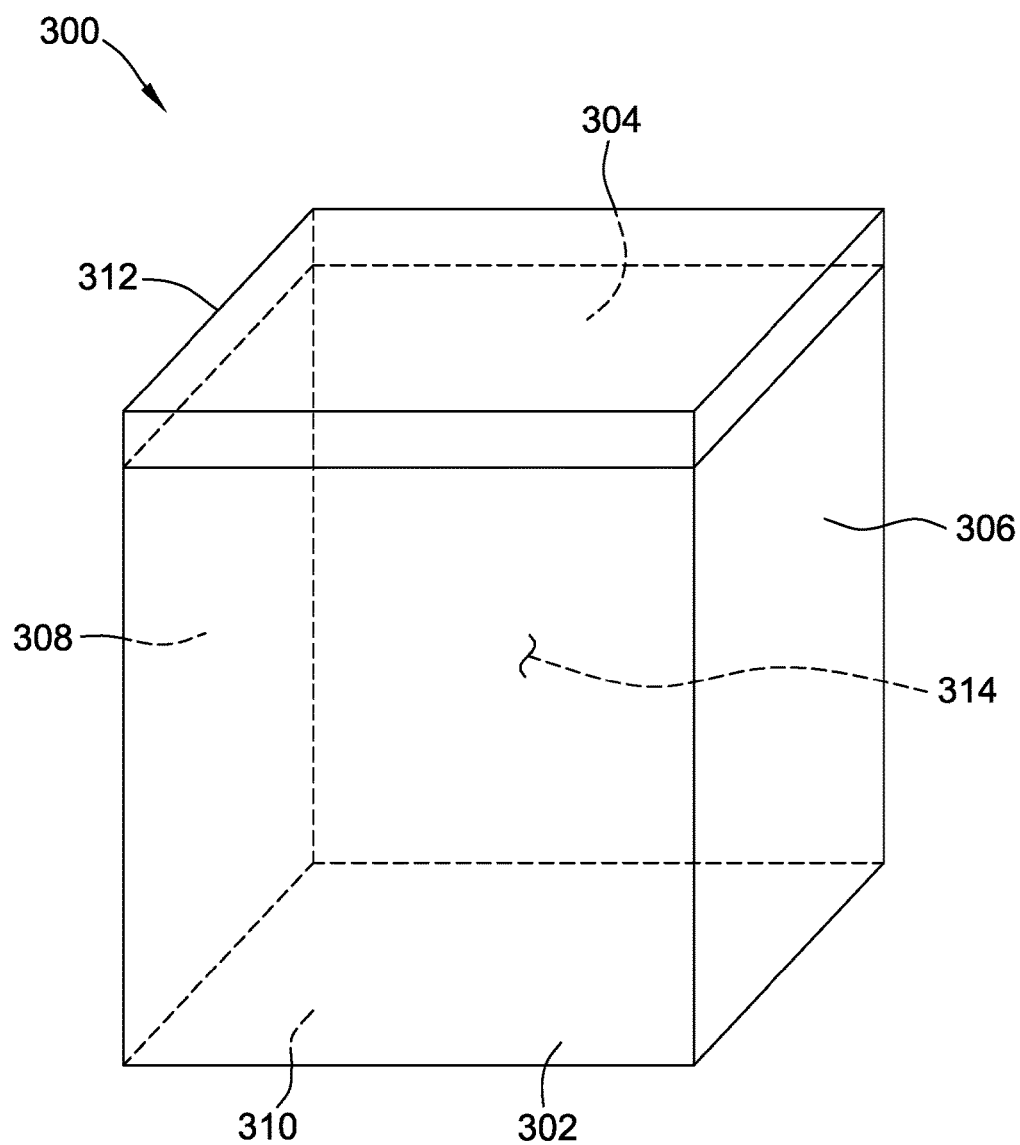
FIG. 4 is a perspective view of a food storage container at least partially formed from the antimicrobial article shown in FIG. 1.

FIG. 4 is a perspective view of a food storage container 300 at least partially formed from antimicrobial article 100 (shown in FIG. 1). In the exemplary embodiment, container 300 includes a front wall 302, a rear wall 304, a first sidewall 306, a second sidewall 308, a bottom wall 310, and a cover 312. Walls 302-312 together define a cavity 314 within container 300 in which food is meant to be stored. In the exemplary embodiment, container 300 includes removable cover 312. Alternatively, container 300 is a five-sided container not having a cover. Generally, container 300 is any structure in which food may be placed for storage and preservation.

In the exemplary embodiment, each of walls 302-312 is formed from antimicrobial article 100 such that any food placed within cavity 314 is surrounded by antimicrobial article 100. Alternatively, fewer than all of walls 302-312 are formed from antimicrobial article 100. For example, in one embodiment, only bottom wall 310 is formed from antimicrobial article 100. In such a configuration, any other walls of container 300 are formed from any material. Generally, at least one of walls 302-312 is formed from antimicrobial article.

In operation, food meant for consumption, or any other perishable item, is placed within container 300 having at least one of walls 302-312 formed from antimicrobial article 100. The "halo effect" of antimicrobial article 100, as described above, effectively neutralizes a majority of the pathogens that cause the food items to begin to decay. As such, food items stored in container 300 decay at a much slower rate than when not exposed to the "halo effect" of antimicrobial article 100, and food items with a relatively short shelf life, such as fruits, may be stored in container 300 in an edible state for a much longer period of time before consumption.

Figure 5:
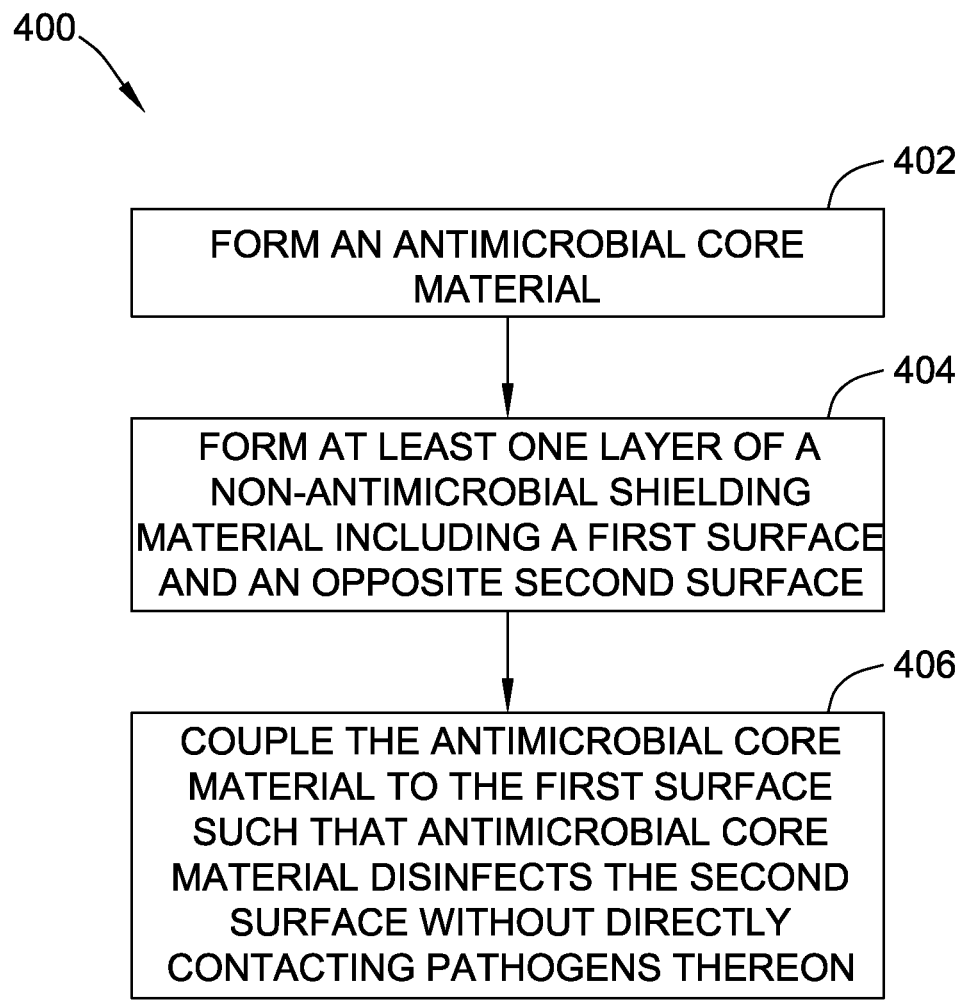
FIG. 5 is a flow diagram of a method of disinfecting a surface using the antimicrobial article.

FIG. 5 is a flow diagram of a method 400 of disinfecting a surface using an antimicrobial article, such as antimicrobial article 100 (shown in FIGS. 1-3). Method 400 includes forming 402 an antimicrobial core material, such as antimicrobial core 102 (shown in FIG. 2), and forming 404 at least one layer of a non-antimicrobial shielding material, such as non-antimicrobial shield 104 (shown in FIG. 2), including a first surface and an opposite second surface, such as surfaces 112 and 114 (shown in FIG. 2). Method 400 also includes coupling 406 the antimicrobial core to the first surface such that the antimicrobial core disinfects the second surface without contacting pathogens thereon.

EXPERIMENTAL DATA

A prototype of the antimicrobial article described above utilizing an antimicrobial alloy core of at least 70% copper core, and cladded with stainless 316L alloy was tested by an independent testing laboratory using the pathogen *Staphylococcus aureus* ATCC 6538, which may also be known as "MRSA". The results showed the pathogen strain was reduced by 99% in approx. 100 minutes on the prototype antimicrobial article. The pathogen did not have direct contact with the copper alloy core, and yet was neutralized by the "halo effect". This is in contrast to the common convention in the industry that the "halo effect" is effectively blocked by any shielding material placed between the antimicrobial alloy and the pathogen to protect the alloy.

In the experiment, three metal plate samples: 1) titanium, 2) stainless steel clad copper and nickel antimicrobial alloy, and 3) exposed copper and nickel antimicrobial alloy were exposed to *Staphylococcus aureus* ATCC 6538 for a time period of 24 hours and measurements of the number of pathogen cells remaining were conducted at regular time periods. Table 1 below illustrates the results:

| Time (Hrs) | Sample 1 | Sample 2 | Sample 3 |
| --- | --- | --- | --- |
| T = 0 | >1,200 | >1200 | >1200 |
| T = 1 | >1,200 | >1200 | <0.25 |
| T = 2 | >1200 | 370 | <0.25 |
| T = 3 | 920 | 9.9 | <0.25 |
| T = 24 | <0.25 | <0.25 | <0.25 |

As shown in Table 1, at relatively low population densities (<4,000 cells), Sample 3, the exposed copper and nickel antimicrobial alloy, showed significant population reduction of *Staphylococcus aureus* strain ATCC 6538. Specifically, Sample 3 showed a greater than 4000-fold reduction in the population at one hour. At two hours, Sample 2, the stainless steel clad copper and nickel antimicrobial alloy, also showed significant anti-pathogen activity reducing the number of *Staphylococcus aureus* strain ATCC 6538 cells by more than three-fold. At three hours, the 10 μL droplets of pathogen-containing fluid were visibly evaporating and the titanium metal (Sample 1) was also showing a decrease in pathogen cells most likely due to dehydration. No evidence of MRSA was obtained at 24 hours from the beginning of the experiment. Although contained in covered dishes, no additional humidification of the chambers was performed. These tests were conducted at a constant 27° C. (80.6° F.).

The above described antimicrobial article facilitates efficient methods of disinfecting a surface. Specifically, in contrast to many known antimicrobial articles, the antimicrobial article described herein includes an antimicrobial core coupled to a non-antimicrobial shield configured to protect the core from exposure to external elements. The antimicrobial core includes an antimicrobial property due to a "halo effect" from electromagnetic energy produced by the protected antimicrobial core that disinfects, within a relatively short period of time, a surface of the non-antimicrobial shield opposite the antimicrobial core without the core directly contacting the pathogens located on the shield surface. The antimicrobial core includes an alloy of at least 50% of any combination of antimicrobial copper/copper alloys, gold, silver, and molybdenum, with the remaining portion of the core including a non-antimicrobial alloy, such as nickel or zinc. The non-antimicrobial shield is fabricated from a non-antimicrobial material, such as, but not limited to stainless steel and serves as a protective layer to the antimicrobial core providing strength, physical and chemical durability, and stainless qualities.

By effectively eliminating harmful pathogens from a surface of a protective material coupled to the antimicrobial core without directly contacting the pathogens, the above described antimicrobial article exploits the benefits of the "halo effect" provided by the antimicrobial core alloy, and yet still provides durability and chemical resistance qualities of stainless steel to shield the antimicrobial core.

Exemplary embodiments of methods, systems, and apparatus for using an antimicrobial article are not limited to the specific embodiments described herein, but rather, components of articles and steps of the methods may be utilized independently and separately from other components and steps described herein. For example, the antimicrobial article may be used in combination with other application environments and in other procedures, and is not limited to practice with the systems or methods described herein. Rather, the exemplary antimicrobial article can be implemented and utilized in connection with many other applications, equipment, and systems that may benefit from the advantages described herein.

Although specific features of various embodiments of the disclosure may be shown in some drawings and not in others, this is for convenience only. In accordance with the principles of the disclosure, any feature of a drawing may be referenced and claimed in combination with any feature of any other drawing.

This written description uses examples to disclose various embodiments, which include the best mode, to enable any person skilled in the art to practice those embodiments, including making and using any devices or systems and performing any incorporated methods. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An article comprising:
   a first layer of a shielding material comprising a first surface and an opposite second surface, wherein said shielding material comprises stainless steel; and
   a core material comprising molybdenum coupled to said first surface, wherein said core material is an antimicrobial material configured to eliminate pathogens located on said second surface without contacting the pathogens.

2. The article in accordance with claim 1, wherein the shielding material is a non-antimicrobial material, said article further comprising a second layer of non-antimicrobial shielding material coupled to said antimicrobial core material opposite said first layer.

3. The article in accordance with claim 1, wherein said shielding material encases said core material such that said core material is not exposed to the ambient surroundings.

4. The article in accordance with claim 1, wherein said shielding material comprises between approximately 10% to approximately 99% by weight of a total material of said article.

5. The article in accordance with claim 1, wherein said core material comprises an antimicrobial alloy comprising an antimicrobial active component and an inactive component, said antimicrobial active component comprises molybdenum, and said inactive component comprises at least one of zinc and nickel.

6. The article in accordance with claim 5, wherein said active component comprises at least 50% by weight of a total material of said core material.

7. The article in accordance with claim 5, wherein said core material comprises between approximately 10% to approximately 90% by weight of a total material of said article.

8. A food storage container comprising a plurality of walls defining a cavity configured to receive a food item therein, at least one of said plurality of walls comprising:
   a first layer of a non-antimicrobial shielding material comprising a first surface and an opposite second surface;
   an antimicrobial core material comprising molybdenum coupled to said first surface, said antimicrobial core material configured to eliminate pathogens located on said second surface, wherein said first layer of shielding material and said antimicrobial core combine to form an antimicrobial article.

9. The food storage container in accordance with claim 8 further comprising a removable cover.

10. The food storage container in accordance with claim 8, wherein each of said plurality of walls is formed from said antimicrobial article.

11. The food storage container in accordance with claim 8, wherein said non-antimicrobial shielding material encases said antimicrobial core material such that said antimicrobial core material is not exposed to the ambient surroundings.

12. The food storage container in accordance with claim 8, wherein said antimicrobial core material comprises an antimicrobial alloy comprising an antimicrobial active component and a non-antimicrobial inactive component, wherein said antimicrobial active component comprises molybdenum, and wherein said inactive component comprises at least one of zinc and nickel.

13. The food storage container in accordance with claim 8, wherein said antimicrobial core comprises between approximately 10% to approximately 90% by weight of a total material of said antimicrobial article.

* * * * *